(12) United States Patent
Nakamura et al.

(10) Patent No.: US 6,495,328 B2
(45) Date of Patent: Dec. 17, 2002

(54) SUBSTRATE FOR DETECTING BASE SEQUENCES, METHOD OF MANUFACTURING THE SUBSTRATE, AND METHOD OF DETECTING BASE SEQUENCES USING THE SUBSTRATE

(75) Inventors: Fumio Nakamura, Tokyo (JP); Masahiko Hara, Wako (JP)

(73) Assignee: Riken, Wako (JP)

(*) Notice: Subject to any disclaimer, the term of this patent is extended or adjusted under 35 U.S.C. 154(b) by 0 days.

(21) Appl. No.: 09/853,948

(22) Filed: May 11, 2001

(65) Prior Publication Data

US 2001/0055768 A1 Dec. 27, 2001

(30) Foreign Application Priority Data

May 30, 2000  (JP) ........................................ 2000-161289
Mar. 14, 2001 (JP) ........................................ 2001-073028

(51) Int. Cl.[7] .......................... C12Q 1/68; C07H 19/00; C07H 21/00; C07H 21/02
(52) U.S. Cl. ......................... 435/6; 536/22.1; 536/23.1; 536/24.3
(58) Field of Search ............................ 435/6; 536/22.1, 536/23.1, 24.3

(56) References Cited

PUBLICATIONS

Mol. Cryst. Liq. Cryst., 2000, vol. 349, pp. 219–222; "Immobilization of DNA on Self–Assembled Monolayer" by Fumio Nakamura et al.

AC Research, Anal. Chem. 1997, vol. 69, pp. 4939–4947; "Surface Plasmon Resonance Imaging Measurements of DNA Hybridization Adsorption and Streptavidin/DNA Multilayer Formation at Chemically Modified Gold Surfaces" by Claire E. Jordan et al.

Langmuir 1999, vol. 15, pp. 111–115; "Immobilization of DNA through intercalation at Self–Assembled Monolayers on Gold" by Nobuyuki Higashi et al.

The Society of Polymer Science, Japan: "Polymer Preprints, Japan, vol. 49 No. 1".

The Socity of Polymer Science, Japan: "Polymer Preprints, Japan, vol. 49 No. 3".

*Primary Examiner*—Jezia Riley
(74) *Attorney, Agent, or Firm*—Rosenthal & Osha L.L.P.

(57) ABSTRACT

A substrate for detecting base sequences that comprises a transparent support, a thin metal film formed on one side of the transparent support, and a self-assembled monolayer with a nonionic aromatic compound being an intercalator of nucleic acid polymers dispersed over the surface formed on the metal film. The substrate is manufactured, for example, by immersing a transparent support with a thin gold film formed on one side in a solution that contains a disulfide (S—S) compound containing anthracene for the intercalator of nucleic acid polymers form on the metal film. A nucleic acid polymer (probe or target) is immobilized to the monolayer of the substrate, another nucleic acid polymer (target or probe) is hybridized to the nucleic acid polymer immobilized to the monolayer, and the results of the hybridization can be detected by the Surface Plasmon Resonance method after washing.

20 Claims, 4 Drawing Sheets

Fig.1(a) Formation of self-assembled monolayer

Fig.1(b) Immobilization of single-stranded DNA (probe)

Fig.1(c) Hybridization of complementary DNA (target)

SUBSTRATE FOR DETECTING BASE SEQUENCES, METHOD OF MANUFACTURING THE SUBSTRATE, AND METHOD OF DETECTING BASE SEQUENCES USING THE SUBSTRATE

FIELD OF THE INVENTION

The present invention relates to the technology for determining the base sequences of DNA and RNA, which are the materials that carry the genetic information in life forms, particularly to the technology for determining base sequences by hybridization.

BACKGROUND

The hybridization method that uses for the probe a single-stranded nucleic acid polymer complementary to the sequence of a region of the target nucleic acid polymer is known as a method of detecting a specific genetic sequence in nucleic acid polymers such as DNA or determining whether two nucleic acid polymers are identical.

By the hybridization method, a target nucleic acid polymer is immobilized to a support such as a glass slide or silicon chip, and an aqueous solution containing a probe nucleic acid polymer labeled with a radioisotope (RI) or fluorescent substance is placed on the film. If the probes hybridize to the target nucleic acid polymer, only the hybridized probes remain on the film after washing. The presence of a specific sequence in the target nucleic acid polymer can be determined by detecting the radiation or fluorescence from the IR or fluorescent substance label of the probes or the color of the precipitate.

The radioactive labeling method requires a considerable cost and labor for the facility for handling radioactive substances and its management. The method also has a health problem of people who handle radioactive substances. For this reason, the method that uses fluorescent substances for labeling and performs detection using a fluorescence detection system is in common use grin recent years.

However, a special modification treatment which takes a lot of time and labor is needed to label nucleic acid polymer probes with a fluorescent substance. Moreover, the fading of the fluorescent substance inevitably occurs because of irradiation of the exciting light, and hence an expensive dedicated fluorescence detection system is needed for a high-accuracy measurement.

Further, the immobilization efficiency of a target nucleic acid polymer is very low, and a large amount of a target nucleic acid polymer is needed for immobilization. Therefore, fluorescence detection is difficult when only a small amount of target nucleic acid polymers can be obtained.

There is another method that immobilizes single-stranded nucleic acid polymer probes directly to a solid support, hybridizes a target nucleic acid polymer with the probes, and performs the detection using the Plasmon Resonance method or Quartz Oscillator method. This method of detecting base sequences also has problems that a modification of nucleic acid polymers is required to immobilize them to the support and that the control of immobilization is difficult.

SUMMARY OF THE INVENTION

The present invention was made under the situation described above. The object of the present invention is therefore to provide an improved substrate for detecting base sequences and method of detecting base sequences using the substrate which can control the immobilization efficiency of a probe or target nucleic acid polymer to the substrate at a best condition for hybridization and consequently can detect the base sequence of a target nucleic acid polymer from a very small amount of the target nucleic acid polymer without need of leveling nucleic acid polymers with isotopes or fluorescent substances and without need of modifying the molecular structure of nucleic acid polymers.

The substrate for detecting base sequences of the present invention comprises a transparent support, a thin metal film formed on one side of the transparent support, and a self-assembled monolayer with a nonionic aromatic compound (such as anthracene, pyrene, naphthalene, phenanthrene and naphthene) being an intercalator of nucleic acid polymers dispersed over the surface formed on the metal film.

The method of manufacturing the substrate for detecting base sequences comprises the following steps: synthesizing a compound (such as a disulfide compound and thiol compound) containing a nonionic aromatic compound that is an intercalator of nucleic acid polymers; and immersing a transparent support with a thin metal film formed on one side in a solution containing the compound to let the self-assembled monolayer with the nonionic aromatic compound dispersed over the surface formed on the metal film.

The method of manufacturing the substrate for detecting base sequences that has a self-assembled monolayer with anthracene dispersed over the surface comprises the following steps: synthesizing a disulfide compound containing anthracene for the intercalator of nucleic acid polymers; and immersing a transparent support with a thin metal film formed on one side in a solution containing the compound to let a self-assembled monolayer of disulfide with anthracene dispersed over the surface form on the surface of the support.

The method of manufacturing the substrate above for detecting base sequences that has a self-assembled monolayer with pyrene dispersed over the surface comprises the following steps: synthesizing a thiol compound containing pyrene for the intercalator of nucleic acid polymers; and immersing a transparent support with a thin metal film formed on one side in a solution containing the compound to let a self-assembled monolayer of thiol with pyrene dispersed over the surface form on the surface of the support.

The method of detecting base sequences using the substrate comprises the following steps: letting the self-assembled monolayer adsorb a nucleic acid polymer (probe or target) to immobilize the nucleic acid polymer to the substrate; and performing the hybridization of another nucleic acid polymer (target or probe) and the nucleic acid polymer immobilized to the substrate on the substrate.

DESCRIPTION OF PREFERRED EMBODIMENTS

Preferred embodiments of the present invention are described below referring to the drawings.

FIRST EMBODIMENT

Figure 1A:
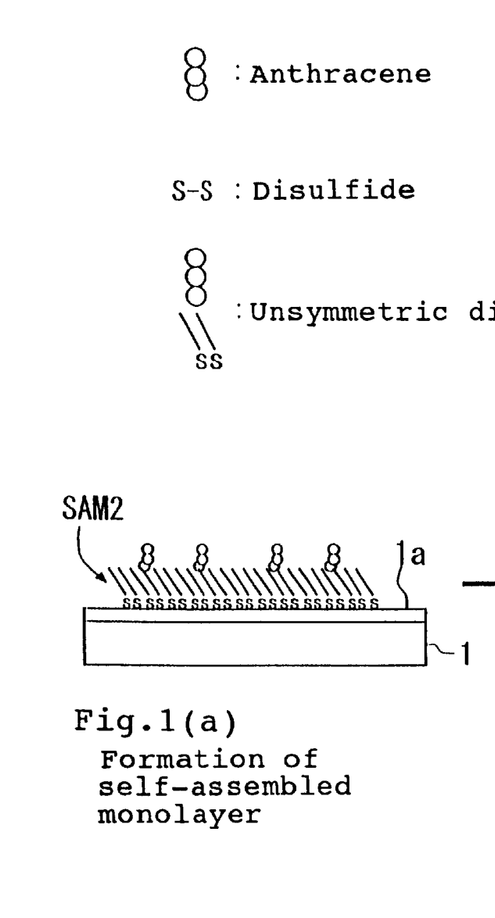
FIGS. 1(a) to 1(c) show an overview of the process of the method of detecting a base sequence of DNA according to the present invention.
Figure 1B:
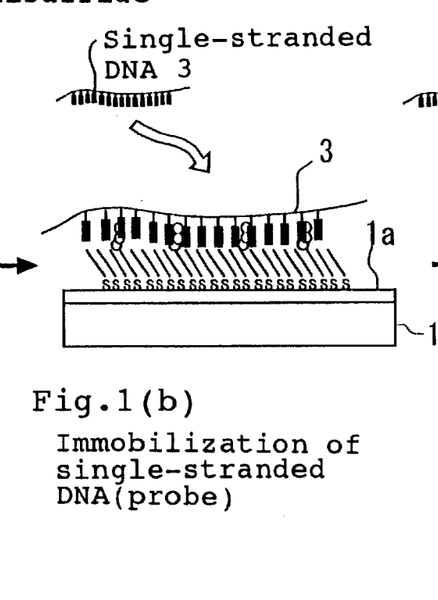
Figure 1C:
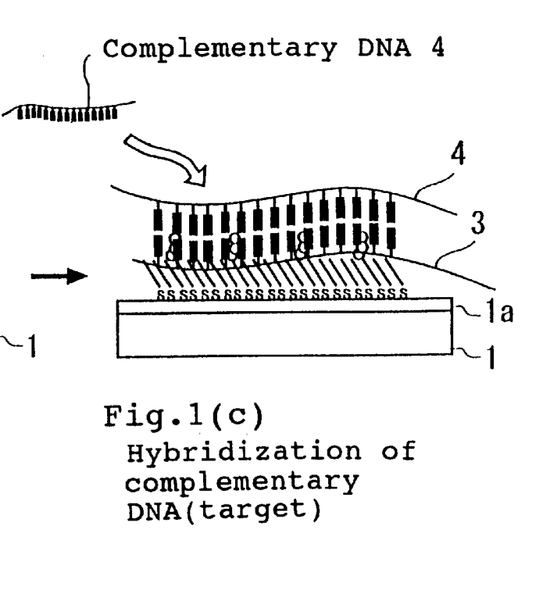

FIG. 1 schematically shows an overview of the steps for detecting the base sequence of nucleic acid polymers according to the present invention.

(a) Formation of self-assembled monolayer (SAM)

A transparent support 1 with one side coated with a thin gold film la is immersed in a solution that contains a disulfide (S—S) compound containing anthracene. A SAM 2 of the disulfide containing anthracene forms over the gold film la during this step. There are two compounds present in the SAM 2: one in which an anthracene is bound to S (sulfur) with a chain of alkyls between and another with no anthracene binding with the ends.

(b) Immobilization of single-stranded DNA (probe) to the SAM

A probe DNA 3 is immobilized to the SAM by placing an aqueous solution containing the probe DNA 3 on the SAM 2 and letting the SAM 2 adsorb the probe DNA 3.

(c) Hybridization of complementary DNA (target)

An aqueous solution containing a target DNA 4 is placed on the SAM 2 to hybridize the target DNA 4 to the probe DNA 3. After the steps above, the substrate is washed with water. As the result, only the target DNA 4 hybridizing to the probe DNA 3 remains on the SAM 2. The base sequence of the target DNA 4 therefore can be known by detecting the target DNA 4 remaining on the SAM 2.

Since the present invention immobilizes a probe DNA to the SAM 2 that is formed as described above, it becomes possible to increase the immobilization efficiency of the probe DNA to the substrate and consequently to detect the base sequence of a target DNA 4 even when only a very small amount of the target DNA 4 can be obtained.

The immobilization efficiency of the probe DNA 3 to the SAM can be controlled by adjusting the ratio of the number of anthracene to the number of the sulfur atoms of the SAM 2. Specifically, the adjustment of the ratio can be performed by appropriately determining the mixing ratio of the compounds represented by the chemical formulas 1 and 2:

Chemical formula 1 where x, y and z are all within the range from 6 through 18, and R is $CH_3$, OH or $NH_2$.

The aforementioned ratio is preferably within the range from 10% through 50%. If the ratio is below 10%, it is difficult for the SAM 2 to adsorb the probe DNA 3. If the ratio is greater than 50%, the adsorption efficiency of the probe DNA 3 to the SAM 2 is too large, and the hybridization of the probe DNA 3 and the target DNA 4 becomes difficult to occur. The ratio is more preferably within the range from 15% to 20%.

The ratio of the number of the anthracene to that of the sulfur atoms in the compound of the chemical formula 1 is 1:2. Therefore, if the SAM 2 is formed of the compound of the chemical formula 1 alone, the ratio of the number of anthracene to the number of the sulfur atoms in the SAM 2 is 50%.

Further, the SAM 2 with the ratio of the number of anthracene to the number of the sulfur atoms smaller than 50% can be obtained by forming the SAM 2 adding an appropriate amount of the compound of the chemical formula 2 to the compound of the chemical formula 1. If the SAM 2 is formed of a mixture of the compound of the chemical formula 1 and that of the chemical formula 2 at a mixing ratio of 99:1, the ratio of the number of anthracene to the number of the sulfur atoms in the SAM 2 is about 15% in the SAM 2.

For the method of detecting the target DNA 4 remaining on the SAM 2, a widely used method that labels the target DNA 4 with a fluorescent substance. However, the detection can be performed more quickly by using the Surface Plasmon Resonance method.

Figure 2A:
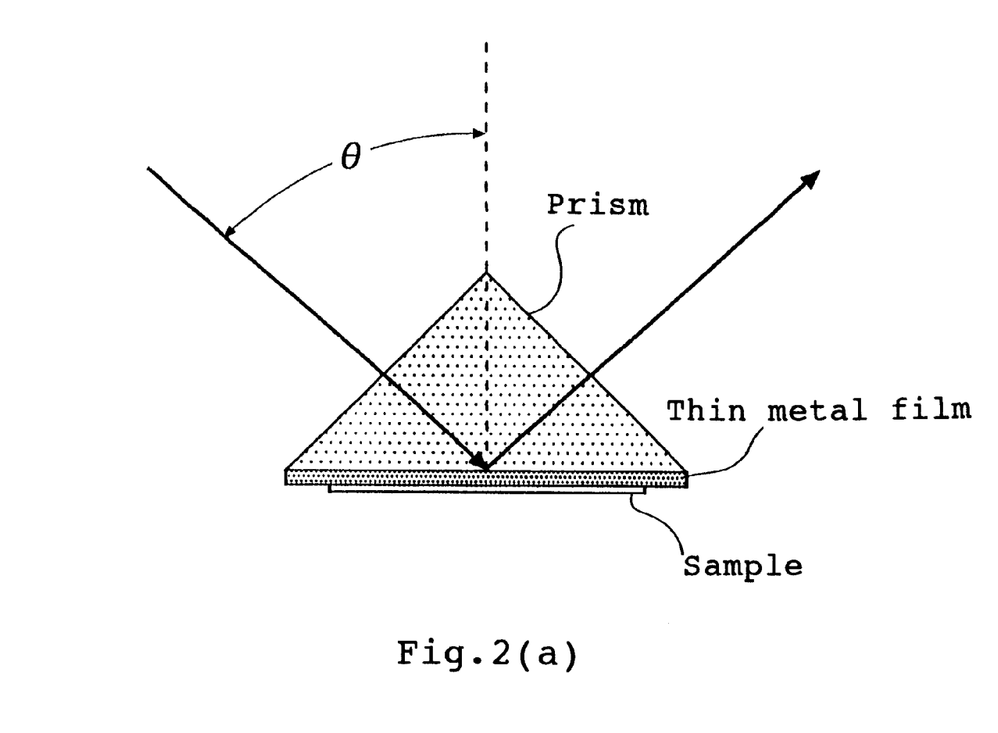
FIG. 2(a) shows the principle of measurement by the Surface Plasmon Resonance method.
Figure 2B:
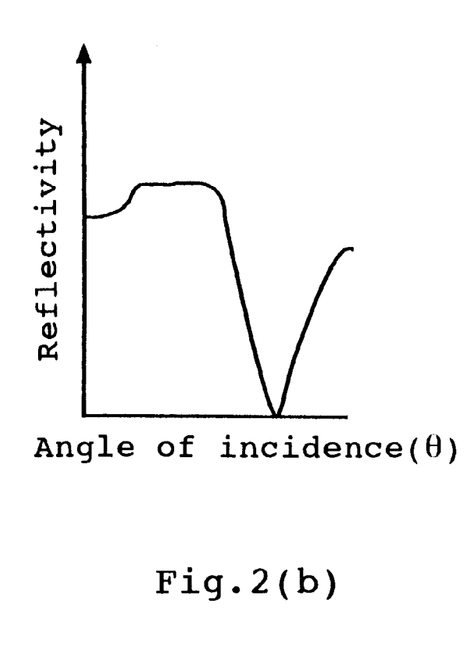
FIG. 2(b) shows the relationship between the angle of incidence (θ) of laser light and the reflectivity measured by the Surface Plasmon Resonance method.

FIG. 2 shows the principle of measurement by the Surface Plasmon Resonance method. As shown in FIG. 2(a), the Surface Plasmon Resonance method uses a transparent support such as a prism with a thin gold or silver layer formed on one side of the support (bottom side in the example shown), deposits a sample on the metal film, and sheds laser light to the metal film obliquely through the transparent material. The relationship between the angle of incidence (θ) of the laser light and the reflectivity is shown in FIG. 2(b). A deep valley observed by the measurement corresponds to the Surface Plasmon Resonance.

The Surface Plasmon Resonance is greatly dependent on the boundary condition on the thin metal film. The thickness and surface coverage of a very this film adsorbed on the metal film can be known by simulating the angle of incidence—reflectivity curve.

In this embodiment, therefore, the target DNA 4 remaining on the SAM 2 can be quickly and reliably detected by a sensitized detection of the difference between the reflectivity in the case in which the target DNA 4 is present on the SAM 2 and that in the case in which the target DNA 4 is not present on the SAM 2.

Figure 3:
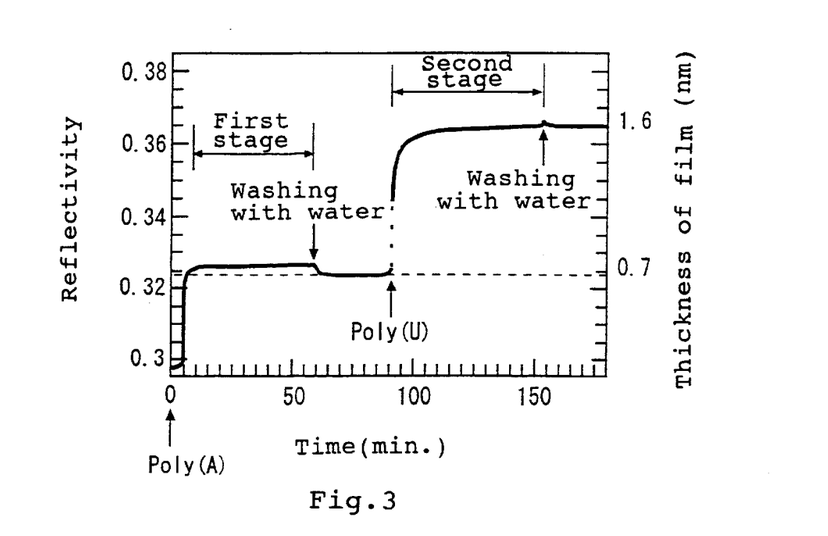
FIG. 3 shows an example of the result of measurement by the Surface Plasmon Resonance method during the process of RNA adsorption to a self-assembled monolayer of a disulfide containing anthracene and hybridization (change in the reflectivity and the thickness of the film plotted over time).

FIG. 3 shows an example of the result of the observation of the process of RNA adsorption to the SAM of a disulfide containing anthracene by the Surface Plasmon Resonance method.

The substrate for this experiment was made by synthesizing a disulfide compound containing an anthracene that is a DNA intercalator (chemical formula 3 below), dissolving the compound island 11-mercapto-1-undecanol (chemical formula 4 below) in chloroform at a ratio of 99:1, and immersing a support with a thin gold film formed on the bottom side in the solution for 24 hours to let a SAM form on the gold film. The substrate obtained was used to immobilizing RNA.

Chemical formula 3

(Anth-C11-SS-C8)

In this example, Poly(A) (polyadenylic acid) was adsorbed to the SAM at the first stage, and Poly(U) (polyuridilic acid) complementary to Poly(A) was added at the second stage. Adsorption of Poly(U) was also observed, but adsorption of RNA other than Poly(U) was not observed. This observation shows a specific interaction between Poly (A) and Poly(U) on the SAM.

It is known from this results of the experiment that the method of the present invention can also be applied to the detection of the base sequence of RNA.

SECOND EMBODIMENT

Although anthracene is used for the intercalator of nucleic acid polymers in the above embodiment, pyrene can also be used instead of anthracene.

In the case where pyrene is used, the base sequence of a target DNA can be detected by the same process of FIG. 1. Further, it is also possible to increase the immobilization efficiency of a probe DNA to the substrate, and hence the base sequence of a target DNA can be detected even when only a very small amount of the target DNA can be obtained.

The immobilization efficiency of the probe DNA 3 to the SAM 2 can be controlled by appropriately determining the ratio of the number of pyrene to the number of the sulfur atoms of the SAM 2. Specifically, the adjustment of the ratio can be performed by appropriately determining the mixing ratio of the compounds represented by the chemical formulas 5 and 6:

Chemical formula 5 where x and z are within the range from 6 through 18, and R is OH, $CH_3$ or $NH_2$.

The ratio of the number of pyrene to that of the sulfur atoms is preferably within the range from 15% through 50%. If the ratio is below 15%, it is difficult for the SAM to adsorb a probe DNA. If the ratio is greater than 50%, the adsorption efficiency of a probe DNA to the SAM 2 is too large, and the hybridization of the probe DNA and a target DNA becomes difficult to occur. The ratio is more preferably within the range from 15% to 20%.

The ratio of the number of pyrene to that of the sulfur atoms in the compound of the chemical formula 5 is 1:1. Therefore, if the SAM 2 is formed of the compound of the chemical formula 5 alone, the ratio of the number of pyrene to the number of the sulfur atoms in the SAM 2 is 100%.

Further, the SAM 2 with the ratio of the number of pyrene to the number of the sulfur atoms smaller than 100% can be obtained by forming the SAM 2 adding an appropriate amount of the compound of the chemical formula 6 to the compound of the chemical formula 5. If the SAM 2 is formed of a mixture of the compound of the chemical formula 5 and that of the chemical formula 6 at a mixing ratio of 1:1, the ratio of the number of pyrene to the number of the sulfur atoms in the SAM 2 is about 50% in the SAM 2.

For the method of detecting the target DNA 4 remaining on the SAM 2, a widely used method that labels the target DNA 4 with a fluorescent substance. However, the detection can be performed more quickly by using the Surface Plasmon Resonance method for this embodiment.

Figure 4:
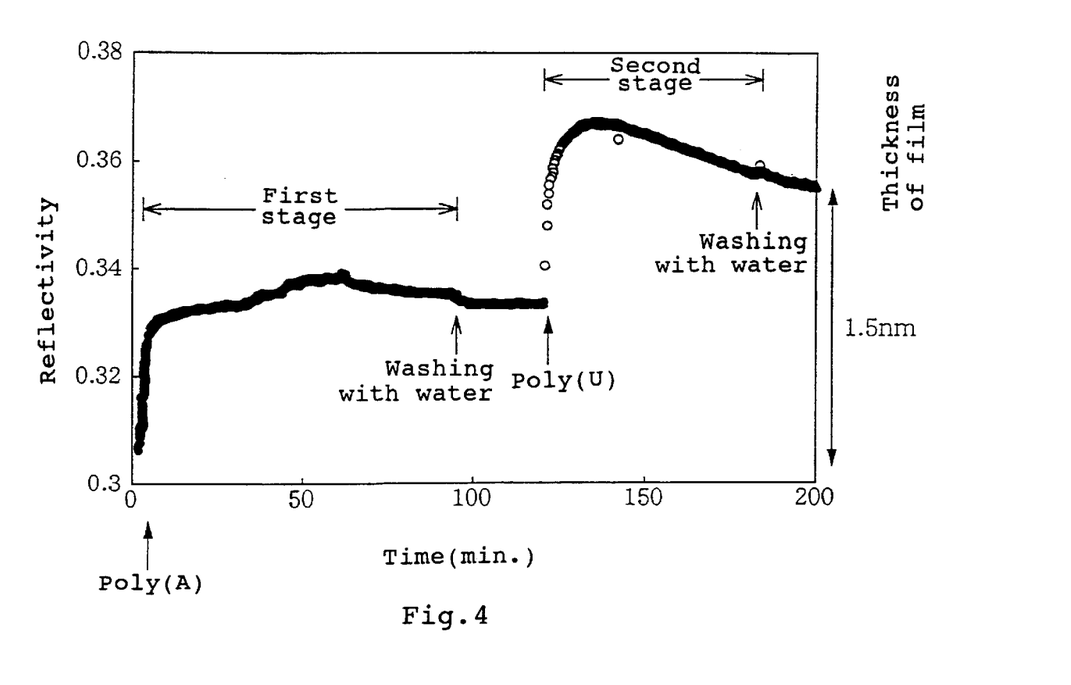
FIG. 4 shows an example of the result of measurement by the Surface Plasmon Resonance method during the process of RNA adsorption to a self-assembled monolayer of a disulfide containing pyrene and hybridization (change in the reflectivity and the thickness of the film plotted over time).

FIG. 4 shows an example of the observation of the process of RNA adsorption to a SAM of thiol containing pyrene by the Surface Plasmon Resonance method.

The substrate for this experiment was made by synthesizing a thiol compound containing pyrene that is a DNA intercalator (chemical formula 7 below), dissolving the compound and mercaptoundecanol (chemical formula 8 below) in chloroform at a ratio of 1:1, and immersing a support with a thin gold film formed on the bottom side in the solution for 24 hours to let a SAM form on the gold film. The substrate obtained was used to immobilizing RNA.

Chemical formula 7

From a comparison between FIG. 3 and FIG. 4, the adsorbing capability of pyrene in the first stage, or the stage for letting the SAM adsorb Poly (A), is higher than that of anthracene. This means that a single-strand RNA can be immobilized with a stronger adsorption by using pyrene.

Figure 5A:
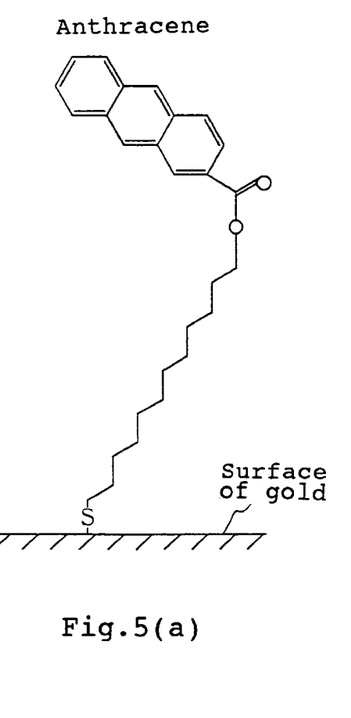
FIG. 5(a) shows the shape of a disulfide molecule containing anthracene in the self-assembled monolayer formed on a support.
Figure 5B:
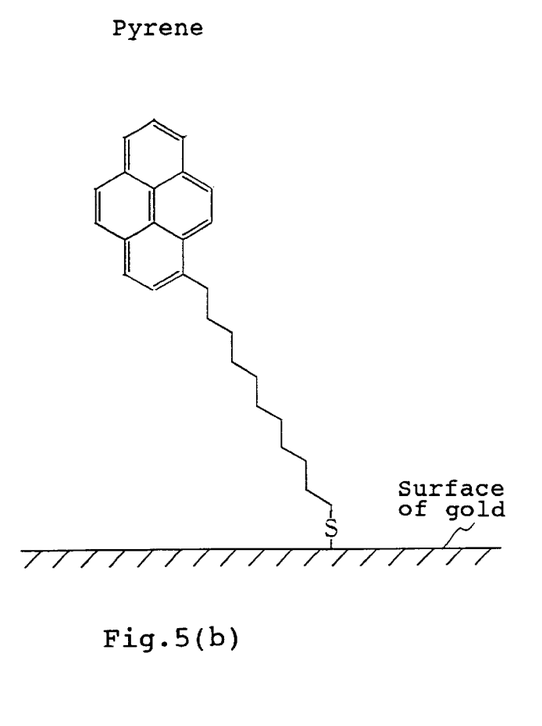
FIG. 5(b) shows the shape of a thiol molecule containing pyrene in the self-assembled monolayer formed on a support.

Further, from the results of an IR-RAS measurement of SAMs, the anthracene molecule in a disulfide containing anthracene greatly tilts with respect to the surface of the SAM as shown in FIG. 5(a), whereas the pyrene molecule of a disulfide containing pyrene is approximately perpendicular to the surface of the SAM as shown in FIG. 5(b). It is therefore possible to immobilize more DNA or RNA on the substrate by using a SAM of a thiol containing pyrene than by using a SAM of a disulfide containing anthracene.

Although the above embodiments use anthracene or pyrene for the DNA intercalator are described above, other nonionic aromatic compounds such as naphthalene, phenanthrene or naphthene can be used.

Further, the Surface Plasmon Resonance method was used for detecting the probe nucleic polymer and target nucleic polymer remaining on the SAM in the above embodiments, but the Quartz Oscillator method may also be used.

Moreover, a SAM of disulfide or thiol containing anthracene or pyrene was formed on a gold film formed on a transparent support SAM in the above embodiments, but Si, Al, Ag, Cu, and other metals, their alloys (including alloys with gold) and oxides can also be used for the material for the thin metal film. Gold and silver are most preferable for the material for the thin metal film from the point of view of utilizing the adsorbing capability of the sulfur atoms contained in organic compounds as well as from the point of view of using the Surface Plasmon Resonance method and the Quartz Oscillator method.

As understood from the above description, it becomes possible to control the immobilization efficiency of a probe or target nucleic acid polymer to the substrate at a best condition for hybridization and consequently to detect the base sequence of a target nucleic acid polymer from a very small amount of the target nucleic acid polymer without need of leveling nucleic acid polymers with isotopes or fluorescent substances and without need of modifying the molecular structure of nucleic acid polymers, by the substrate and method of detecting base sequences of the present invention.

It will be appreciated that the above descriptions are intended only to serve as examples, and that many other modification and variations are possible within the spirit and the scope of the present invention.

What is claimed is:

1. A substrate for detecting base sequences by hybridization, comprising:
   a transparent support;
   a thin metal film formed on one side of the transparent support;
   a self-assembled monolayer of a nonionic aromatic compound that is an intercalator of nucleic acid polymers, the self-assembled monolayer formed over a surface of the thin metal film; and
   a single-stranded nucleic acid probe bound to the self-assembled monolayer.

2. A method of manufacturing a substrate for detecting base sequences by hybridization, comprising:
   preparing a solution comprising a nonionic aromatic compound that is an intercalator of nucleic acid polymers;
   immersing a transparent support with a thin metal film formed on one side of the transparent support in the solution to let a self-assembled monolayer of the nonionic aromatic compound form over a surface of the thin metal film; and
   binding a single-stranded nucleic acid probe to the self-assembled monolayer.

3. The substrate of claim 1, wherein the nonionic aromatic compound comprises an anthracene moiety.

4. The substrate of claim 3, wherein the nonionic aromatic compound further comprises a disulfide moiety, and wherein a ratio of a number of the anthracene moieties to a number of sulfur atoms in said self-assembled monolayer is within a range from 10% to 50%.

5. The substrate of claim 3, wherein the nonionic aromatic compound further comprises a disulfide moiety, and wherein a ratio of a number of the anthracene moieties to a number of sulfur atoms in said self-assembled monolayer is within a range from 15% to 20%.

6. A method of manufacturing a substrate for detecting base sequences, comprising:
   preparing a solution of a disulfide compound comprising an anthracene moiety as an intercalator of nucleic acid polymers;
   immersing a transparent support with a thin metal film formed on one side of the transparent support in the solution to let a self-assembled monolayer form on the thin metal film; and
   binding a single-stranded nucleic acid probe to the self-assembled monolayer.

7. The method of claim 6, wherein a ratio of a number of the anthracene moieties to a number of sulfur atoms in said self-assembled monolayer is within a range from 10% to 50%.

8. The method of claim 6, wherein a ratio of a number of the anthracene moieties to a number of sulfur atoms in said self-assembled monolayer is within a range from 15% to 20%.

9. The method of claim 7, wherein said ratio is adjusted by mixing a compound represented by chemical formula 1 and a compound represented by chemical formula 2:

Chemical Formula 1

Chemical Formula 2 where x, y and z are all within a range from 6 to 18, and R is $CH_3$, $OH$ or $NH_2$.

10. The substrate of claim 1, wherein the nonionic aromatic compound comprises a pyrene moiety.

11. The substrate of claim 10, wherein the nonionic aromatic compound further comprises a thiol moiety, and wherein a ratio of a number of the pyrene moieties to a number of sulfur atoms in said self-assembled monolayer is within a range from 5% to 100%.

12. The substrate of claim 10, wherein the nonionic aromatic compound further comprises a thiol moiety, and wherein a ratio of a number of the pyrene moieties to a number of sulfur atoms in said self-assembled monolayer is within a range from 15% to 50%.

13. A method of manufacturing a substrate for detecting base sequences, comprising:
   preparing a solution comprising a thiol compound comprising a pyrene moiety as an intercalator of nucleic acid polymers;
   immersing a transparent support with a thin metal film formed on one side of the transparent support in the solution of said thiol compound to let a self-assembled monolayer form on the thin metal film; and
   binding a single-stranded nucleic acid probe to the self-assembled monolayer.

14. The method of claim 13, wherein a ratio of a number of the pyrene moieties to a number of sulfur atoms in said self-assembled monolayer is within a range from 5% to 100%.

15. The method of claim 13, wherein a ratio of a number of the pyrene moieties to a number of sulfur atoms in said self-assembled monolayer is within a range from 15% to 50%.

16. The method of claim 14, wherein said ratio is adjusted by mixing a compound represented by chemical formula 5 and a compound represented by chemical formula 6:

Chemical Formula 5

-continued

Chemical Formula 6 where x and z are both within a range from 6 to 18, and R is $CH_3$, OH or $NH_2$.

17. A method of detecting a base sequence, characterized by performing the hybridization of said probe nucleic acid polymer and a target nucleic acid polymer on the substrate of any of claims 2, 4 to 7, or 11 to 14.

18. A method of detecting a base sequence, comprising:
   binding a single-stranded nucleic acid probe to a self-assembled monolayer formed on a surface of a metal thin film coated on one side of a transparent support, the self-assembled monolayer comprising a nonionic aromatic intercalator of nucleic acid polymers;
   hybridizing a target nucleic acid polymer to the single-stranded nucleic acid probe on the self-assembled monolayer; and
   detecting the target nucleic acid polymer hybridized to the single-stranded nucleic acid probe using a Surface Plasmon Resonance method or a Quartz Oscillator method.

19. The method of claims 8, wherein said ratio is adjusted by mixing a compound represented by chemical formula 1 and a compound represented by chemical formula 2:

Chemical Formula 1

-continued

Chemical Formula 2 where x, y and z are all within a range from 6 to 18, and R is $CH_3$, OH or $NH_2$.

20. The method of claim 15, wherein said ration is adjusted by mixing a compound represented by chemical formula 5 and a compound represented by chemical formula 6:

Chemical Formula 5

Chemical Formula 6 where x and z are both within a range from 6 to 18, and R is $CH_3$, OH or $NH_2$.

* * * * *

UNITED STATES PATENT AND TRADEMARK OFFICE
CERTIFICATE OF CORRECTION

PATENT NO. : 6,495,328 B2
DATED : December 17, 2002
INVENTOR(S) : Fumio Nakamura et al.

It is certified that error appears in the above-identified patent and that said Letters Patent is hereby corrected as shown below:

<u>Column 9,</u>
Lines 7-10, delete Claim 17 in its entirety

Signed and Sealed this

Twenty-ninth Day of April, 2003

JAMES E. ROGAN
*Director of the United States Patent and Trademark Office*